(12) United States Patent
Amiot et al.

(10) Patent No.: US 8,449,551 B2
(45) Date of Patent: May 28, 2013

(54) DEVICE, METHOD AND SYSTEM FOR DIGITIZING POSITION AND ORIENTATION INFORMATION OF HIP JOINT IMPLANT COMPONENTS

(75) Inventors: Louis-Philippe Amiot, Hampstead (CA); Herbert André Jansen, Montréal (CA); Isabelle Fontaine, Vancouver (CA); Daniel Odermatt, Montréal (CA)

(73) Assignee: Orthosoft Inc., Montreal (CA)

( * ) Notice: Subject to any disclaimer, the term of this patent is extended or adjusted under 35 U.S.C. 154(b) by 77 days.

(21) Appl. No.: 13/165,822

(22) Filed: Jun. 22, 2011

(65) Prior Publication Data

US 2011/0251835 A1 Oct. 13, 2011

Related U.S. Application Data

(62) Division of application No. 10/570,630, filed as application No. PCT/CA2004/001638 on Sep. 7, 2004, now abandoned.

(30) Foreign Application Priority Data

Sep. 4, 2003 (CA) ..................................... 2439850

(51) Int. Cl.
*A61B 17/58* (2006.01)
*A61B 17/60* (2006.01)
*A61F 2/00* (2006.01)
(52) U.S. Cl.
USPC .......... 606/91; 606/86 R; 606/102; 623/22.12
(58) Field of Classification Search
USPC ........... 606/89, 91, 99, 102; 623/22.11–23.38
See application file for complete search history.

(56) References Cited

U.S. PATENT DOCUMENTS

| 4,475,549 A | 10/1984 | Oh |
| 5,879,401 A | 3/1999 | Besemer et al. |

(Continued)

FOREIGN PATENT DOCUMENTS

| WO | 0267783 | 9/2002 |
| WO | WO9319382 | 9/2003 |
| WO | WO2004030556 | 4/2004 |

OTHER PUBLICATIONS

Zheng, Guoyan; Marx, Axel; ;Langlotz, Ulrich; Widmer, Karl Heinz; Buttaro, Martin; Nolte, Lutz Peter; A Hybrid CT Free Navigation System for Total Hip Arthroplasty; published online in Wiley InterScience (www.interscience.wiley.com); 2002.

(Continued)

*Primary Examiner* — Andrew Yang
(74) *Attorney, Agent, or Firm* — Norton Rose Canada LLP

(57) ABSTRACT

A device (10,10',20,20') for digitizing a center of rotation of a hip joint implant component (A,F) with respect to a bone element in computer-assisted surgery. The device (10,10',20, 20') comprises a detectable member (12,22) trackable for position and orientation by a computer-assisted surgery system (30). A body (11,21) is connected to the detectable member (12,22) in a known geometry. The body (11,21) has a coupling portion (14,14',24,25) adapted to be coupled to the hip joint implant component (A,F) in a predetermined configuration. The center of rotation of the hip joint implant component (A,F) is calculable in the predetermined configuration as a function of the known geometry and of the position and orientation of the detectable member (12,22).

6 Claims, 3 Drawing Sheets

U.S. PATENT DOCUMENTS

| | | | |
|---|---|---|---|
| 6,711,431 B2 * | 3/2004 | Sarin et al. | 600/426 |
| 7,634,306 B2 | 12/2009 | Sarin et al. | |
| 2004/0077940 A1 | 4/2004 | Kienzle, III et al. | |
| 2004/0143340 A1 | 7/2004 | Tuma et al. | |

OTHER PUBLICATIONS

Hamadouche, Moussa; Boutin, Pierre; Daussange, Jacques; Bolander, Mark E.; Sedel, Laurent; Alumina on Alumina Total Hip Arthroplasty; Journal of Bone and Joint Surgery, Inc.; 2002.

Jaramaz, Branislav; Digioia III, Anthony M.; Blackwell, Mike; Nikou, Constantinos; Computer Assisted Measurement of Cup Placement in Total Hip Replacement; Clinical Orthopaedics & Related Research; 1998.

Digioia III, Anthony M.; Jaramaz, Branislav; Plakseychuk, Anton Y.; Moody, Jr., James E.; Nikou, Constantinos; La Barca, Richard S.; Levison, Timothy J.; Picard, Frederic; Comparison of a Mechanical Acetabular Alignment Guide with Computer Placement of the Socket; The Journal of Arthroplasty, vol. 17, No. 3; 2002.

Draft document: Guidance Document for Femoral Stem Prostheses; Orthopedic Devices Branch, Division of General and Restorative Devices, Center for Devices and Radiological Health, U.S. Food and Drug Administration, Aug. 1, 1995.

\* cited by examiner

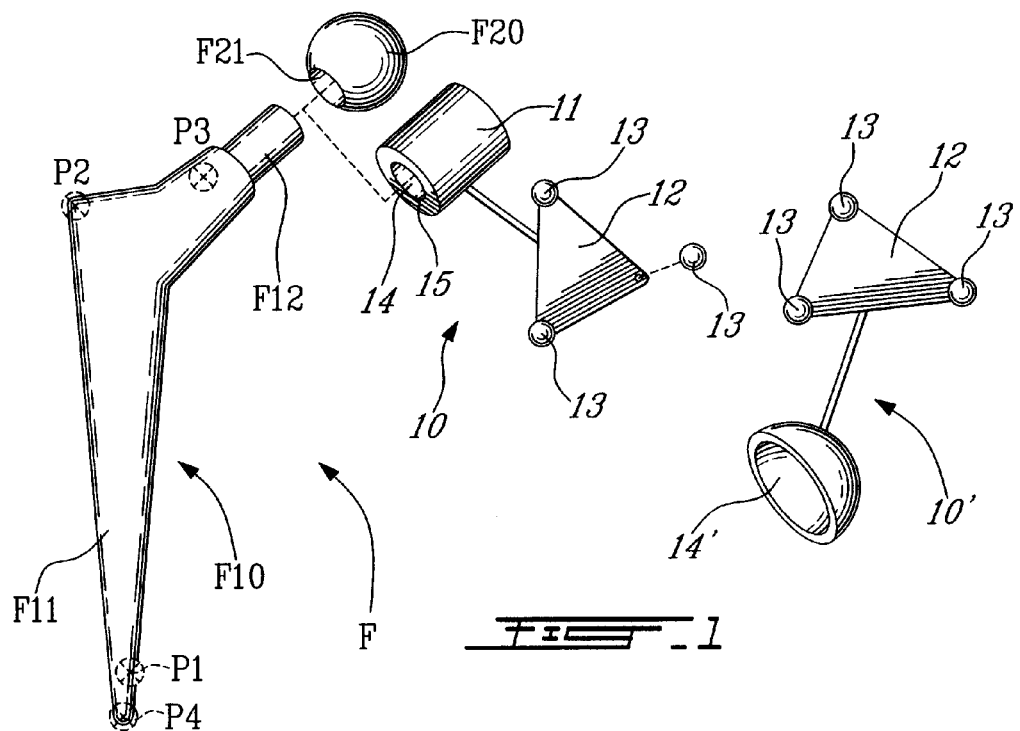
FIG_1
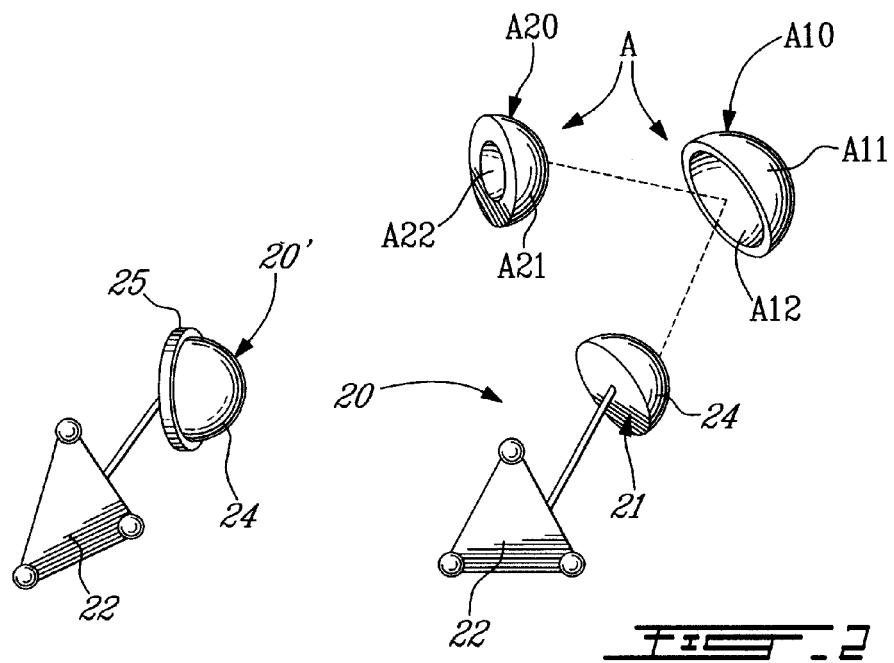
FIG_2

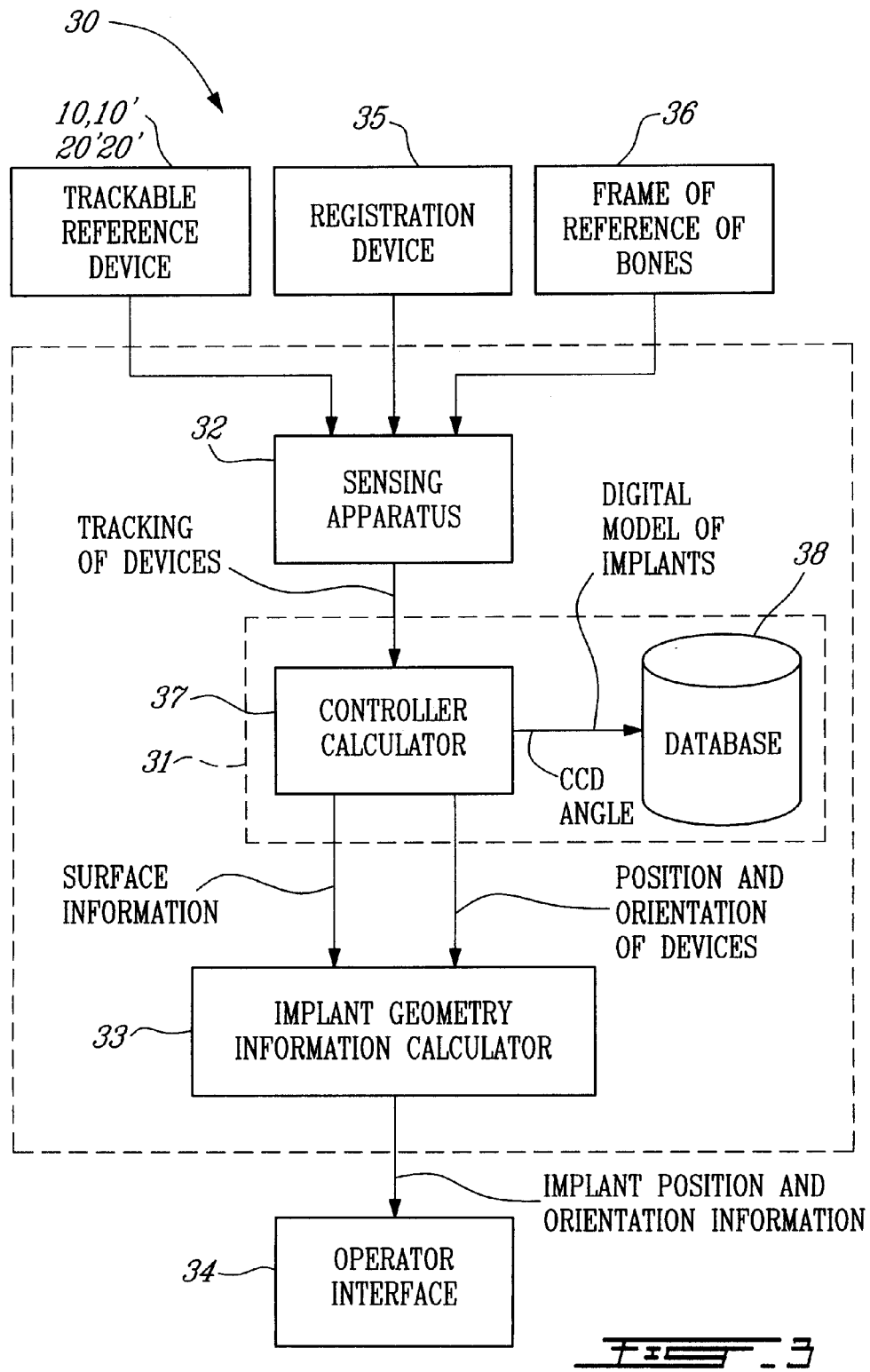

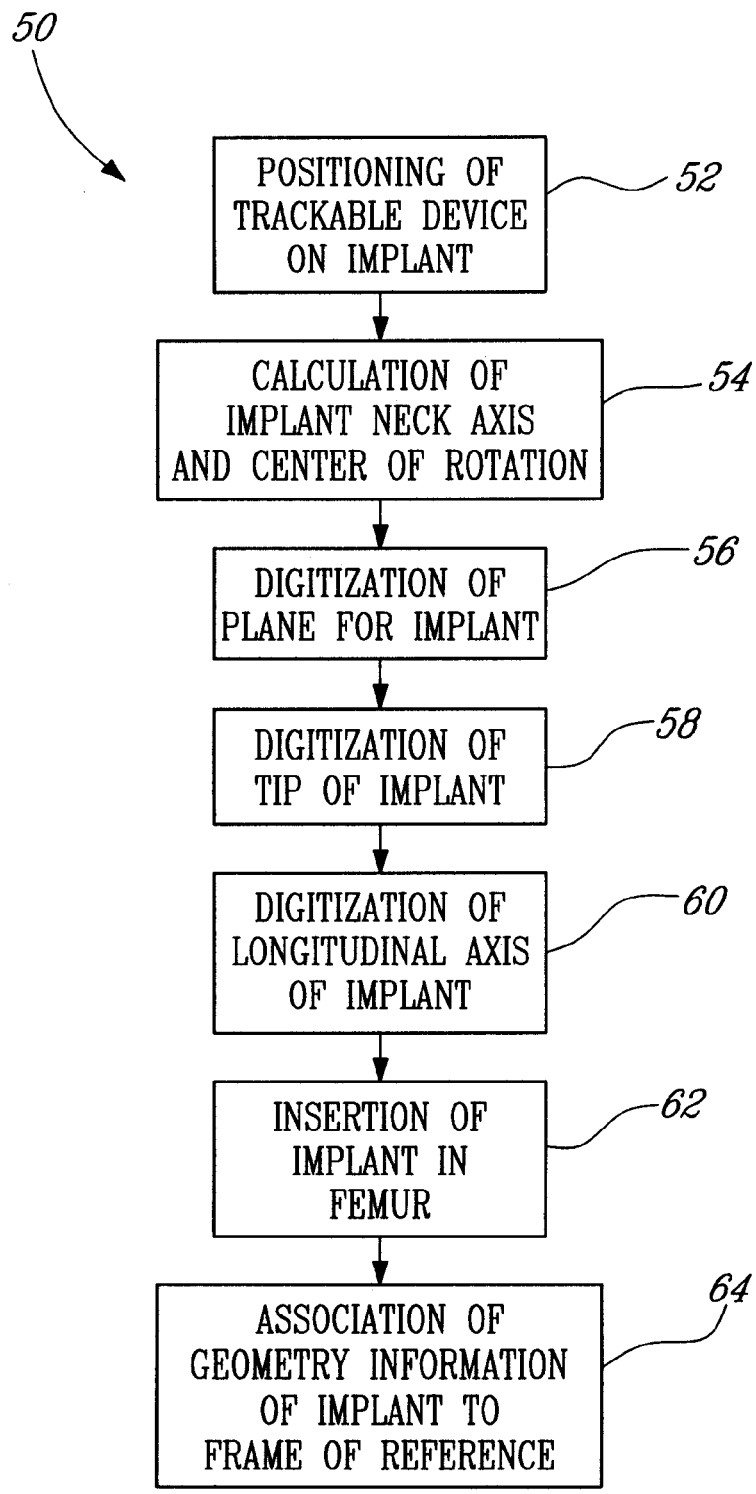

US 8,449,551 B2

DEVICE, METHOD AND SYSTEM FOR DIGITIZING POSITION AND ORIENTATION INFORMATION OF HIP JOINT IMPLANT COMPONENTS

CROSS-REFERENCE TO RELATED APPLICATIONS

The present patent application is a divisional of U.S. application Ser. No. 10/570,630, filed on Mar. 3, 2006, now abandoned which is a United States national-phase entry of International Patent Application No. PCT/CA2004/001638, bearing an international filing date of Sep. 7, 2004, and claiming priority on Canadian Patent Application No. 2,439,850, filed on Sep. 4, 2003.

FIELD OF THE INVENTION

The present invention generally relates to computer-assisted hip replacement surgery and, more particularly, to a device for positioning hip joint implant components during surgery, and to a system and method associated with the device.

BACKGROUND OF THE INVENTION

Computer-assisted surgery (CAS) systems provide position and orientation information in different forms throughout the operative steps, to guide the surgeon in his/her decision making. CAS systems are used for instance to assist surgeons in hip replacement surgery. In hip replacement surgery, the hip joint implants being implanted must assure a desired posture to the patient. Accordingly, the position and orientation information provided to the surgeon must be precise and accurate to obtain the desired posture.

The femoral implant and the acetabular implant generally form a spherical joint, in which the center of a ball head of the femoral implant coincides with the center of an hemispherical socket of the acetabular implant, at a center of rotation of the hip joint implant. During surgery, the femur is separated from its associated pelvis for the implants to be implanted. Through the separation of the femur from the pelvis, position and orientation information is still provided from the tracking of the femur, the pelvis and the various tools being used. For instance, a rasping tool altering the intramedullary canal of the femur may be tracked such that the center of rotation of the femoral implant (i.e., the center of the ball head) may be calculated as a function of the geometry of the femoral implant and of the altered intramedullary canal.

Some types of femoral implants come separate with the ball head being fixable to the femoral implant body. The femoral implant body has a frusto-conical connector end (e.g., a Morse 12/14 taper) upon which the ball head is slid in a friction fit. In calculating the position of the center of rotation of the femoral implant, some precision is lost considering that the fit between the ball head and the frusto-conical connector end is unpredictable to some extent.

Alternatively, it may be desired to confirm the position and orientation of the femoral implant. Referring to the above-described example in which the center of rotation of the femoral implant is calculated as a function of the geometry of the femoral implant and of the altered intramedullary canal, it is possible that the femoral implant is not completely fitted as expected in the altered intramedullary canal. In such a case, a confirmation of the position and orientation of the femoral implant would be appropriate.

SUMMARY OF THE INVENTION

Accordingly, an object of the present invention is to provide a device for obtaining position information for hip joint implant components in computer-assisted surgery.

It is a further object of the present invention to provide a method and system for obtaining position information for hip joint implant components in computer-assisted surgery.

It is a further object of the present invention to provide a device for obtaining the center of rotation of an implant.

It is a further object of the present invention to provide a method for obtaining the center of rotation of an implant.

Therefore, in accordance with the present application, there is provided a device for digitizing a center of rotation of a hip joint implant component with respect to a bone element in computer-assisted surgery, comprising a detectable member trackable for position and orientation by a computer-assisted surgery system; and a body connected to the detectable member in a known geometry, the body having a coupling portion adapted to be coupled to the hip joint implant component in a predetermined configuration, the center of rotation of the hip joint implant component being calculable in the predetermined configuration as a function of the known geometry and of the position and orientation of the detectable member.

Further in accordance with the present invention, there is provided a method for digitizing a center of rotation of a pelvic implant component with a computer-assisted surgery system, comprising the steps of providing a device being trackable for position and orientation by the computer-assisted surgery system, the device being releasably coupled in a known configuration to the pelvic implant component; tracking a position and orientation of a pelvis implanted with the pelvic implant component and a position and orientation of the device; and calculating a center of rotation of the pelvic implant component with respect to the position and orientation of the pelvis by relating the known configuration of the device with the position and orientation tracking of the pelvis and of the device.

Still further in accordance with the present invention, there is provided a method of doing surgical treatment with a position tracking system in computer-assisted surgery for guiding an operator in inserting a femoral implant of a hip joint implant in a resected femur tracked for position and orientation, comprising the steps of positioning a trackable device on the femoral implant in a predetermined configuration, the trackable device being trackable in space for position and orientation; registering implant geometry information for the femoral implant with respect to the trackable device as a function of said predetermined configuration between the femoral implant and the trackable device; and inserting the femoral implant in the femur by obtaining implant position and orientation information, the implant position and orientation information being calculated from said implant geometry information as a function of the tracking for position and orientation of the trackable device with respect to a frame of reference of the femur.

Still further in accordance with the present invention, there is provided a computer-assisted surgery system for guiding an operator in inserting a femoral implant of a hip joint implant in a resected femur tracked for position and orientation, comprising a trackable reference device positionable onto the femoral implant in a predetermined configuration and trackable in space for position and orientation; a registration device trackable in space for position and orientation and handled by the operator to register surface information; a sensing apparatus, for tracking any one of the devices for position and orientation; a controller connected to the sensing apparatus, the controller being provided to: i) calculate a position and orientation of the devices as a function of the tracking by the sensing apparatus; ii) digitize surface information of the femoral implant as a function of the tracking of the registration device by the sensing apparatus; and an implant geometry information calculator connected to the controller, for calculating geometry information of the femoral implant from said predetermined configuration with respect to the trackable reference device, as a function of said surface information of the femoral implant; whereby the geometry information is used to provide implant position and orientation information related to a frame of reference of the femur, so as to guide the operator in subsequently inserting the femoral implant in the resected femur.

BRIEF DESCRIPTION OF DRAWINGS

These and other features, aspects and advantages of the present invention will become better understood with regard to the following description and accompanying drawings wherein:

FIG. 1 is a perspective view of a device for digitizing position and orientation information of a femoral implant, in accordance with a preferred embodiment of the present invention;

FIG. 2 is a perspective view of a device for digitizing position information of an acetabular implant, in accordance with a preferred embodiment of the present invention;

FIG. 3 is a block diagram of a computer-assisted surgery system to be used with the devices of FIGS. 1 and 2; and FIG. 4 is a flow chart illustrating a method of doing surgical treatment for guiding an operator in inserting a femoral implant in a resected femur in hip replacement surgery in accordance with an embodiment of the present invention.

DESCRIPTION OF THE PREFERRED EMBODIMENT

Referring to the drawings and, more particularly, to FIG. 1, a device to be used for obtaining position and orientation information for a femoral implant is generally shown at 10. A femoral implant is shown at F, and has a body F10 and a ball head F20. The body F10 has a stem portion F11, which is adapted to be received in an intramedullary canal of a resected femur (not shown). A connector end F12 projects from an end of the stem portion F11. The connector end F12 is illustrated having a frusto-conical shape, for instance having a Morse 12/14 taper.

The ball head F20 has a spherical outer surface, and a connector bore F21. The connector bore F21 is illustrated having a frusto-conical shape, so as to correspond to the shape of the connector end F12 of the body F10. When the body F10 is suitably received in the intramedullary canal of the femur, the ball head F20 is secured to the connector end F12, by the complementary shapes of the connector end F12 and the connector bore F21.

As mentioned previously, the position of the center of rotation of the femoral implant F is useful information, even prior to the ball head F20 being secured thereto. From the calculated center of rotation, it may be required to further alter the intramedullary canal in view of an anticipated leg length discrepancy. Alternatively, the calculated center of rotation may be used to calculate the size of ball head F20 to be used in the femoral implant F. Femoral implant orientation information is useful in calculating information such as the varus/valgus angle and the offset.

Accordingly, the device 10 is to be used in digitizing the center of rotation of the femoral implant F and/or the orientation of the femoral implant F. The device 10 has a tubular body 11. A tracker base 12 projects from the tubular body 11. The illustrated tracker base 12 is of the type that receives the passive type of tracker, i.e., in the form of three detectable devices 13 in a known geometrical pattern. Alternatively, the tracker base 12 could be used to secure an active tracker to the tubular body 11. The tubular body 11 defines a cylindrical bore 14 (i.e., cylindrical receptacle), having a circular edge 15 at its opening in the tubular body 11. The circular edge 15 has a known diameter, and a known position and orientation with respect to the tracker on the tracker base 12.

The device 10 is to be positioned onto the connector end F12 of the femoral implant F. More specifically, the connector end F12 is received in the cylindrical bore 14, such that the circular edge 15 abuts against an outer surface of the connector end F12. In such a position, the cylindrical bore 14 and the connector end F12 will axially align themselves, considering that the connector end F12 is frusto-conically shaped.

Furthermore, the geometric interrelation (i.e., predetermined known configuration) between the connector end F12 and the cylindrical bore 14 allows the calculation of the position and orientation of the taper of the connector end F12 with respect to the tracker of the device 10. This position and orientation information of the connector end F12 may then be used to calculate the anticipated center of the ball head F20 as a function of the size and geometry of the ball head F20. This position and orientation information of the connector end F12 may alternatively be related to a reference tracker on the femur to allow the calculation of navigation information (e.g., offset, varus/valgus angles, limb length discrepancy, etc.)

An alternative method of calculating the center of the ball head F20 is contemplated. A device 10', having the tracker base 12 with the three detectable devices 13 with a hemispherical hole 14' can be positioned directly on the ball head F20 once the ball head F20 is secured to the connector end F12 of the femoral implant F. Ball heads typically come in 3 defined sizes of 22, 28 and 32 mm, whereby the device 10' is typically provided with corresponding diameters for the hemispherical receptacle 14'. Therefore, when the device 10' is mounted onto the ball head F20, the relation between the center of the hemispherical receptacle 14' and the center of the ball head F20 is known (e.g., the centers are coincident), such that the center of the ball head F20 may be established with respect to a frame of reference on the femur. The determination of the position of the center of rotation of the femoral implant F (through the above described procedure) can be accomplished on trial ball heads for the calculation of other parameters (e.g., limb length), as well as on the definitive ball head F20 installed on the femoral implant F.

It is also contemplated to provide an alignment mechanism between the implants F and/or A and the devices 10 (10') and 20 (20'), respectively, for the interconnection between the implant and its associated device to be reproducible in position and orientation.

Referring to FIG. 2, an alternative embodiment of the device, to be used to obtain position and orientation information for an acetabular implant is generally shown at 20. An acetabular implant is shown at A and has a shell A10 and a liner A20. The shell A10 has a cup-shaped body having an outer surface A11 and a receiving cavity A12. The acetabular implant A is to be fitted into an acetabulum (not shown), with the outer surface A11 being in contact with a surface of the acetabulum. The receiving cavity A12 is equipped with connector holes such that an impactor (not shown) can be used to insert the shell A10 into the acetabulum and adjust its position and orientation.

The liner A20 also has a cup-shaped body. The liner A20 is sized so as to fit into the receiving cavity A20 of the shell A10. More specifically, the liner A20 has an outer surface A21 and a socket A22. The outer surface A21 contacts the surface of the receiving cavity A12 when the liner A20 is fitted into the shell A10. The socket A22 will house the ball head F20 (FIG. 1) of the femoral implant F to form the hip joint implant.

As mentioned previously, the position of the center of rotation of the acetabular implant A (i.e., the center of rotation of the socket A22) is useful information prior to the liner A20 being received in the shell A10. The center of rotation of the acetabular implant A is dependent on the socket size of the liner A20, and on the geometry of the liner A20. The calculated center of rotation of the acetabular implant A can be used for calculating navigation information such as the offset and the limb length discrepancy.

The device 20 is to be used in digitizing the center of rotation of the acetabular implant A. The device 20 has a generally hemispherical body 21. A tracker base 22 projects from an underside of the hemispherical body 21. The illustrated tracker base 22 is of the type that receives the passive type of tracker, i.e., for instance three detectable spheres in a known geometrical pattern. The tracker base 22 could be used to secure an active tracker to the body 21. The hemispherical body 21 defines an outer surface 24.

The device 20 is to be positioned into the receiving cavity A12 of the shell A10 of the acetabular implant A. More specifically, the hemispherical body 21 is sized to fit the receiving cavity A12 of the shell A10, such that the center of rotation of the receiving cavity A12 of the shell A10 may be determined. From the center of rotation of the receiving cavity A12, the center of rotation of the liner A20 may be calculated, knowing the geometry of the liner A20 (e.g., the CAS system being provided with geometry data of various sizes of liners). It is also possible that the liner A20 is of the type having its center coincident with the center of the shell A10. Therefore, the anticipated center of the socket A22 is calculable as a function of the center of the receiving cavity A12 and of the geometry of the liner A20 (stored in the CAS system).

Thereafter, the anticipated center of the rotation of the socket A22 can be related to a reference tracker on the acetabulum to allow the calculation of navigation information, such as the offset and the limb length discrepancy.

It is pointed out that the device 20 may be used to determine the center of rotation of the liner A20 directly. More specifically, the hemispherical body 21 may be sized so as to be received directly in the socket A22 of the liner A20, with the liner A20 having beforehand been secured in the receiving cavity A12. Moreover, an alternative configuration of the device 20, herein illustrated as device 20', is provided with a flange 25 at a periphery of the outer surface 24, so as to enable the calculation of a plane associated to the center of rotation of the acetabular implant A.

The setting of the femoral implant F in the intramedullary canal of the femur is an operation that involves a plurality of factors that will have a direct impact on the success of the hip replacement surgery. Therefore, the setting of the femoral implant F advantageously involves the creation of reference systems that will be used to provide numeric data throughout the surgery to the surgeon for such anatomical references as varus/valgus angle, limb length discrepancy and femoral anteversion. These values are calculable using position and orientation data of the femoral implant, which will be available during the setting of the femoral implant F in the femur.

Therefore, referring to FIG. 4, a method for doing surgical treatment with a tracking system in computer-assisted surgery, for guiding an operator in inserting a femoral implant in a femur as a function of the limb length and the orientation of the femoral implant is generally shown at 50.

The insertion of the femoral implant in the femur takes place after the femoral head has been resected, and the intramedullary canal has been altered in view of the insertion of the implant therein. Such steps are described in International Publication No. WO 2004/030556, published on Apr. 15, 2004, by Jansen et al. At this point, a generic digital model of the implant F is available through the CAS assisting the operator.

In Step 52 of the method 50, the device 10 (FIGS. 1 and 3) is positioned on the connector end F12 of the implant F. If the ball head F20 is already secured to the implant body F10, the device 10' is used (FIGS. 1 and 3).

In Step 54, the orientation of the neck axis of the connector end F12, and the center of rotation of the ball head F20, are calculable as a function of the position and orientation of the tracker base 12.

In Step 56, a plane is digitized for the implant F. More specifically, three non-linear points are digitized using a registration pointer, whereby a plane may be digitized with respect to the device 10 in which all three points lie. For instance, points are taken at P1, P2 and P3 in FIG. 1. With these points and with the neck axis calculated in Step 54, the position and orientation digitized and calculated in Steps 54 and 56 may be associated to the digital model of the implant.

In Step 58, a tip of the implant is digitized with respect to the device 10, using the registration pointer. The tip is illustrated at P4 in FIG. 1.

In Step 60, a longitudinal axis of the implant F is digitized with respect to the device 10. More specifically, the CCD angle of the implant F is generic information provided with the digital model of the implant F. Accordingly, using the neck axis calculated in Step 54 and the CCD angle, a line parallel to the longitudinal axis is defined. The longitudinal axis is then calculated with respect to the device 10 or 10 as being parallel to this line, while lying in the plane digitized in Step 56 and passing through the tip of the implant digitized in Step 58.

In Step 62, now that the required geometry information pertaining to the implant F is known (i.e., longitudinal axis, neck axis, center of rotation, with respect to the device 10), the implant F is inserted in the altered intramedullary canal of the femur F.

Real-time information may be provided to the operator, whereby the device 10 (10') must be kept onto the implant F during the insertion of the implant F in the intramedullary canal. Accordingly, a locking mechanism should be used to secure the device 10 to the implant F in position and orientation.

In Step 64, the geometry information gathered for the implant F is associated to the frame of reference of the femur. By positioning the device 10 (or 10') on the implant F, the position of the center of rotation of the implant F is known, as well as the position of the neck axis.

The orientation of the implant F may be calculated by knowing the interconnection between the implant F and the device 10 (or 10') (through an alignment mechanism, as mentioned previously).

Alternatively, the orientation of the implant F may be calculated using the digital model of the altered intramedullary canal with respect to the frame of reference of the femur, in association with the position and orientation of the device 10 (or 10'). The digital model of the altered intramedullary canal is information available as calculated during the alteration of the intramedullary canal, as described in International Publication No. WO 2004/030556, published on Apr. 15, 2004, by Jansen et al.

Therefore, when the geometry information of the implant F is associated to the frame of reference of the femur, the geometry information can be used to calculate position and orientation information of the implant F with respect to the femur.

For instance, the longitudinal axis of the implant F, as obtained through the method 50, can be used in the calculation of the varus/valgus angle of the femoral implant F. More specifically, the longitudinal axis of the femoral implant is projected onto a frontal plane of the patient along with an axis of the intramedullary canal (as described in International Publication No. WO 2004/030556), with the angle between these two projections representing the varus/valgus angle.

Also, the neck axis of the implant is projected onto the transverse plane (as described in International Publication No. WO 2004/030556), whereby the femoral anteversion is calculable as the angle between this projection and the intersection of the transverse and frontal planes.

Referring to FIG. 3, a CAS system in accordance with the present invention is generally shown at 30. The CAS system 30 has a controller 31 that is connected to the sensing apparatus 32.

The sensing apparatus 32 tracks the devices 10, 10', 20 and 20', as well as a registration device 35 (e.g., registration tool), and frames of reference 36 associated to bones (e.g., femoral and pelvic frames of reference as described in International Publication No. WO 2004/030556). For instance, the sensing apparatus 32 is an optical sensing apparatus that visually detects the position of the passive detectable devices, such as those illustrated at 13 in FIG. 1). The tracking output of the sensing apparatus 32 is calculated as position and orientation of the devices by the controller 31, whereas registered points, as described in Steps 56 and 58 (FIG. 4), are digitized as surface information of the implants.

The CAS system 30 has an implant geometry information calculator 33, that will receive the position and orientation of the devices 10, 10', 20, 20', as well as the surface information, so as to calculate geometry information, as mentioned in Steps 54 and 60, and transfer this data in the form of implant position and orientation information, as described in Step 62, to an operator through operator interface 34.

The controller 31 typically has a controller calculator 37 consisting of a processor that will calculate the above described information, and a database 38 that will hold some information that may be required in the calculation, such as digital model of implants, to which the geometry information and the implant position and orientation information may be associated, as mentioned in the method 50.

The invention claimed is:

1. A method for digitizing a center of rotation of a hip joint implant with a computer-assisted surgery system, comprising:
providing a device being trackable by the computer-assisted surgery system, the device being releasably coupled in a known configuration to an acetabular implant shell of the hip joint implant;
tracking a pelvis implanted with the acetabular implant shell and the device;
calculating at least one of a position and an orientation of the acetabular implant shell with respect to the tracking of the pelvis by relating the known configuration of the device with the tracking of the pelvis and of the device; and
calculating a center of rotation of the hip joint implant using the position and/or orientation of the acetabular implant shell and a digital model of an acetabular implant liner to be inserted into the acetabular implant shell to form the hip joint implant.

2. The method according to claim 1, further comprising calculating an orientation of the hip joint implant with respect to the tracking of the pelvis by relating the known configuration of the device and the digital model of the acetabular implant model, with the position and orientation tracking of the pelvis and of the device.

3. The method according to claim 1, further wherein the digital model is created preoperatively, and comprising obtaining the digital model of the acetabular implant liner from a database.

4. The method according to claim 1, wherein calculating at least one of a position and an orientation of the acetabular implant shell comprises calculating a center of rotation of the acetabular implant shell.

5. The method according to claim 1, further comprising tracking the device as releasably coupled in another known configuration to the acetabular implant liner once formed into the hip joint implant, and further comprising calculating the center of rotation of the hip joint implant using a tracking of the device in the other known configuration.

6. The method according to claim 1, wherein the method is performed on an anatomical bone model or on a cadaver.

* * * * *